United States Patent
Weferling et al.

(10) Patent No.: US 6,242,642 B1
(45) Date of Patent: *Jun. 5, 2001

(54) PROCESS FOR PREPARING ARYLALPHOSPHINIC ACIDS

(75) Inventors: Norbert Weferling, Hürth; Hans-Peter Schmitz, Brühl, both of (DE)

(73) Assignee: Clariant GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/198,538

(22) Filed: Nov. 24, 1998

(30) Foreign Application Priority Data

Nov. 28, 1997 (DE) .............................. 197 52 733
Nov. 10, 1998 (DE) .............................. 198 51 724

(51) Int. Cl.[7] ...................................... C07F 9/30
(52) U.S. Cl. ................................................ 562/8
(58) Field of Search ........................ 562/8; 524/133

(56) References Cited

U.S. PATENT DOCUMENTS

| | | | |
|---|---|---|---|
| 2,957,931 | 10/1960 | Hamilton et al. ............ | 260/403 |
| 3,488,368 | 1/1970 | Spivack ...................... | 260/429.7 |
| 3,534,127 | 10/1970 | Spivack ...................... | 260/968 |
| 3,563,948 | 2/1971 | Spivack ...................... | 260/45.75 |
| 3,742,096 | 6/1973 | Spivack ...................... | 260/953 |
| 3,912,654 | 10/1975 | Heid et al. .................. | 252/321 |
| 3,914,345 | 10/1975 | Kleiner et al. ............... | 260/970 |
| 4,036,811 | 7/1977 | Noetzel et al. ............. | 260/45.75 W |
| 4,185,031 * | 1/1980 | Gillman et al. .............. | 562/26 |
| 4,208,322 | 6/1980 | Sandler ...................... | 260/45.75 K |
| 4,321,187 | 3/1982 | Granzow ..................... | 524/133 |
| 4,590,014 * | 5/1986 | Wolf . | |
| 4,594,199 * | 6/1986 | Thottahil . | |
| 4,632,741 | 12/1986 | Wolf .......................... | 204/157.73 |
| 4,939,285 | 7/1990 | Weis et al. .................. | 558/214 |
| 4,972,011 | 11/1990 | Richardson et al. ......... | 524/133 |
| 4,973,727 | 11/1990 | Gainer et al. ............... | 558/133 |
| 5,780,534 | 7/1998 | Kleiner et al. ............... | 524/133 |

FOREIGN PATENT DOCUMENTS

| | | |
|---|---|---|
| 0327496 | 8/1989 | (EP) . |
| 0699708 | 3/1996 | (EP) . |
| 8505520 | 5/1984 | (ES) . |
| 1 558 606 | 2/1969 | (FR) . |

OTHER PUBLICATIONS

Houben–Weyl, Methoden der organischen Chemie, vol. XII/1, 4th Edition 1963, pp. 228ff.
"Phosphinsäure und deren Derivate," Dr. Felcht, vol. E2, 1982, pp. 123 ff.
CA:120:245501 abs of JP05194562, Aug. 1993.*
Chemical abstracts vol. 64 abstract No. 16661 g by Hoffmann, Jun. 1966.*
CA:107:176590 absBull Chem Soc Jpn by Ohno 60(8) pp2945–51, 1987.*
CA:107:25119 abs of ES 532346, Jun. 1985.*
E.E. Nifant'EV: "Acid catalysis in the hydrophosphorylation of olefins" Journal of General Chemistry USSR., vol. 50, No. 8/1, –Aug. 1980, pp. 1416–1423, XP002093427, New York US.
E.E. Nifant'EV: "Hydrophosphorylation of cyclopentenes" Journal of General Chemistry USSR., vol. 61, No. 1/1, –Jan. 1991 pp. 83–92, XP002093428 New York US.
Chemical Abstracts, vol. 69, No. 16, Oct. 14, 1968 Columbus, OH, US; abstract No. 067487, p. 6310; column 2; XP002093429 & Petrov K.A.: "Dialkylphosphinic acids" Khim. Org. Soedin. Fosfora, Akad. Nauk SSSR, Otd. Obshch. Tekh. Khim., 1967, pp. 181–186, SU.
"Synthesis of DI(n–octyl)phosphinic acid. Influence of the sulfuric acid in the phosphination of 1–octene with sodium hypophosphite,"M. Martinez, C. Herranz, N. Miralles, & A. Sastre, AFINIDAD LIII, 466, 1996, pp. 404–406.
William C. Drinkard: "Some salts of symmetric phosphinic acids" Journal of the American Chemical Society., Bd. 74, Nr. 21, –Nov. 5, 1952 Seiten 5520–5521, XP002093391.

* cited by examiner

*Primary Examiner*—Jean F. Vollano
(74) *Attorney, Agent, or Firm*—Susan S. Jackson; Scott E. Hanf

(57) ABSTRACT

The invention relates to a process for preparing arylalkyiphosphinic acids and/or alkali metal salts thereof by reacting olefins with arylphosphonous acids and/or alkali metal salts thereof, which comprises carrying out the reaction in the presence of a free-radical initiator.

The invention also relates to the use of the products prepared by the abovementioned process for preparing flame retardants.

8 Claims, No Drawings

PROCESS FOR PREPARING ARYLALPHOSPHINIC ACIDS

The invention relates to a process for preparing arylalkylphosphinic acids and/or alkali metal salts thereof by reacting olefins with arylphosphonous acids and/or alkali metal salts thereof and to the use of the compounds prepared by this process.

The addition of carbon-carbon double bonds to phenylphosphonous acid to give phosphinic acid derivatives having two phosphorus-carbon bonds is known in principle, but leads to unsatisfactory yields (Houben-Weyl, Methoden der organischen Chemie [Methods in organic chemistry], Vol. XII/1, 4th Edition 1963, pp. 228 ff, and Vol. E2, 1982, pp. 123 ff). A mixture of reaction products which must be laboriously worked up is also frequently obtained.

In particular, when use is made of olefins which are not activated by electron-withdrawing substituents, such as alpha-olefins, cycloolefins, dienes or cyclodienes, it is not possible by the abovementioned method to prepare the wanted target compounds in yields which are adequate for industrial syntheses.

The object therefore underlying the invention is to provide a process for preparing arylalkylphosphinic acids or alkali metal salts thereof by reacting olefins with arylphosphonous acids and/or alkali metal salts thereof, which process avoids the abovementioned disadvantages and leads to high yields of arylalkylphosphinic acids in short times.

This object is achieved by a process of the type described at the outset which comprises carrying out the reaction in the presence of a free-radical initiator.

Preferably, the olefins are unbranched or branched α-olefins.

Preferably, the olefins are ethylene, propylene, n-butene, isobutene, n-pentene, isopentene, n-hexene, isohexene, n-octene, isooctene, 1-decene, 1-dodecene, 1-tetradecene, 1-hexadecene, n-eicosene, and/or 2,4,4-trimethylpentene isomer mixture.

Preferably, as olefins, use is made of those having an internal double bond, cyclic or open-chain dienes and/or polyenes having from 4 to 20 carbon atoms.

Preferably, the olefins bear a functional group.

Suitable olefins are compounds of the formula

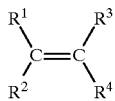

where $R^1$–$R^4$ can be identical or different and are hydrogen, an alkyl group having from 1 to 18 carbon atoms, phenyl, benzyl or alkyl-substituted aromatic systems.

Suitable compounds are likewise cycloolefins of the formula

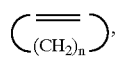

in particular cyclopentene, cyclohexene, cyclooctene and cyclodecene.

Use can also be made of open-chain dienes of the formula

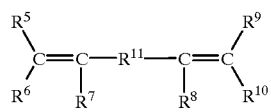

where $R^5$–$R^{10}$ are identical or different and are hydrogen or a $C_1$ to $C_6$ alkyl group and $R^{11}$ is $(CH_2)$n where n=0 to 6. Preference is given in this case to butadiene, isoprene and 1,5-hexadiene.

Preferred cyclodienes are 1,3-cyclopentadiene, dicyclopentadiene and 1,5-cyclooctadiene and norbornadiene.

Preferably, the arylphosphonous acid and/or alkali metal salts thereof are phenylphosphonous acid and/or alkali metal salts thereof.

Preferably, the aryl radical of the arylalkylphosphinic acids and arylphosphonous acids is an aromatic system having from 6 to 12 carbon atoms, which can be monosubstituted or polysubstituted by halogens, hydroxyl, aryl, alkyl, ether, ester, keto, carboxyl, sulfonyl and/or chloroalkyl groups.

Preferably, the free-radical initiator has an azo group, which is cationic or non-cationic.

As cationic free-radical initiators, use is preferably made of 2,2'-azobis(2-amidinopropane) dihydrochloride or 2,2'-azobis(N,N'-dimethyleneisobutyramidine) dihydrochloride.

Compounds which are also suitable according to the invention are non-cationic azo compounds such as azobis (isobutyronitrile), 4,4'-azobis(4-cyanopentanoic acid) and 2,2'-azobis(2-methylbutyronitrile).

Compounds which are likewise suitable according to the invention as free-radical initiators are inorganic peroxide free-radical initiators (hydrogen peroxide, ammonium peroxodisulfate, potassium peroxodisulfate etc.) and/or organic peroxide free-radical initiators (dibenzoyl peroxide, di-tert-butyl peroxide, peracetic acid etc.).

A broad selection of suitable free-radical initiators may be found, for example, in Houben-Weyl, Supplementary Volume 20, in the chapter "Polymerisation durch radikalische Initiierung" [Polymerization by free-radical initiation] on pages 15–74.

Preferably, the reaction is carried out in the presence of carboxylic acids.

Particularly preferably, the carboxylic acid is acetic acid.

Preferably, the reaction is carried out at a temperature of from 40 to 130° C.

Particularly preferably, the reaction is carried out at a temperature of from 60 to 100° C.

In particular, the process is preferably carried out at 5 a temperature of from 80 to 95° C.

Preferably, the reaction is carried out in a pressure reactor. This applies, in particular, when the boiling point of the olefins is below the reaction temperature.

The invention also relates to the use of the arylalkylphosphinic acids and/or alkali metal salts thereof obtained by the process described above for preparing flame retardants.

The invention likewise relates to the use of the arylalkylphosphinic acids and/or alkali metal salts thereof obtained by the process described above for preparing flame retardants for thermoplastic polymers such as poly(ethylene terephthalate), poly(butylene terephthalate), polystyrene or polyamide and for thermosetting plastics.

The arylalkylphosphinic acids and/or alkali metal salts thereof obtained by the process described above are also used as additives in polymeric compounds, as extraction media and surfactants.

The invention is described by the examples below.

EXAMPLE 1

500 g (3.5 mol) of phenylphosphonous acid were charged, together with 4 kg of acetic acid, into a 16 l pressure reactor. Then the mixture was heated with stirring to an internal temperature of 85° C. and ethylene was forced in until saturation was reached at 5 bar. 27 g (100 mmol, equivalent to 3 mol %, based on the phenylphosphonous acid used) of 2,2'-azobis(2-amidinopropane) dihydrochloride, dissolved in 100 ml of water were thereafter metered in over the course of 3 hours. The exothermic reaction was controlled by the metering rate of the abovementioned free-radical initiator solution in such a manner that a maximum reaction temperature of 95° C. was reached. During the further reaction, ethylene was resupplied, so that the pressure over the entire period of the experiment was maintained at about 5 bar. The mixture was then allowed to continue to react for a further 3 h at 85° C. The reactor was then depressurized and cooled. The yield was 4.7 kg (100% of theory).

| $^{31}$P-NMR analysis: | phenylphosphonous acid: | 1.3 mol % |
|---|---|---|
| | phenylethylphosphinic acid: | 85.2 mol % |
| | phenylbutylphosphinic acid: | 10.0 mol % |
| | unknown components: | 3.5 mol % |

EXAMPLE 2

100 g (0.7 mol) of phenylphosphonous acid were heated to 85° C. together with 400 g of glacial acetic acid and 85 g (0.8 mol) of n-octene in a multiple neck flask equipped with agitator, thermometer, dropping funnel and reflux condenser. To this mixture, in the course of one hour, a solution of 6 g (0.022 mol) of 2,2'-azobis(2-amidinopropane) dihydrochloride was added dropwise. The reaction temperature in this period was between 85 and 90° C. The mixture was then allowed to continue to react for a further 4 hours at 85° C. After cooling to room temperature, the contents were analyzed.

| $^{31}$P-NMR analysis: | phenylphosphonous acid: | 2.4 mol % |
|---|---|---|
| | phenyloctylphosphinic acid: | 96.3 mol % |
| | unknown components: | 1.3 mol % |

What is claimed is:

1. A process for preparing phenylalkylphosphinic acids having no halogen substituents, alkali metal salts of the phenylalkylphosphinic acids, or a combination thereof, comprising reacting olefins having no halogen substituents with phenylphosphonous acids, alkali metal salts of the phenylphosphonous acids or a combination thereof wherein the reaction is carried out in the presence of a free-radical initiator containing an azo group.

2. The process as claimed in claim 1, wherein the olefins are ethylene, propylene, n-butene, isobutene, n-pentene, isopentene, n-hexene, or isohexene.

3. The process as claimed in claim 1, wherein the initiator is 2,2'-azobis(2-amidinopropane) dihydrochloride, 2.2'-azobis(2-methylbutyronitrile) or 2,2'-azobis(N,N'-dimethyleneisobutyramidine) dihydrochloride.

4. The process as claimed claim 1, wherein the reaction is carried out in the presence of carboxylic acids.

5. The process as claimed in claim 4, wherein the carboxylic acid is acetic acid.

6. The process as claimed in claim 1, wherein the reaction is carried out at a temperature of from 40 to 130° C.

7. The process as claimed in claim 1, wherein the reaction is carried out at a temperature of from 80 to 130° C.

8. The process as claimed in claim 1, wherein the reaction is carried out in a pressure reactor.

* * * * *